(12) United States Patent
Hooks et al.

(10) Patent No.: US 7,085,481 B2
(45) Date of Patent: Aug. 1, 2006

(54) METHOD AND APPARATUS FOR ADJUSTING THE RATE OF VAPORIZATION

(75) Inventors: Aaron L. Hooks, Warsaw, IN (US); Robert G. Cox, Goshen, IN (US)

(73) Assignee: Dekko Technologies, Inc., North Webster, IN (US)

( * ) Notice: Subject to any disclaimer, the term of this patent is extended or adjusted under 35 U.S.C. 154(b) by 0 days.

(21) Appl. No.: 11/150,398

(22) Filed: Jun. 9, 2005

(65) Prior Publication Data

US 2005/0276583 A1    Dec. 15, 2005

Related U.S. Application Data

(60) Provisional application No. 60/578,663, filed on Jun. 10, 2004.

(51) Int. Cl.
*F24F 6/08*    (2006.01)

(52) U.S. Cl. ............................... 392/395; 392/386
(58) Field of Classification Search .............. None
See application file for complete search history.

(56) References Cited

U.S. PATENT DOCUMENTS 5,647,053 A  *  7/1997  Schroeder et al. .......... 392/390
6,466,739 B1 * 10/2002  Ambrosi et al. ............ 392/395
6,580,875 B1 *  6/2003  Rymer ........................ 392/395

* cited by examiner

*Primary Examiner*—Thor S. Campbell
(74) *Attorney, Agent, or Firm*—Taylor & Aust, P.C.

(57) ABSTRACT

A vaporization device including a housing, a wick, at least one heating element and a rotational coupling. The wick is partially contained within the housing and extends from the housing. The at least one heating element being proximate the wick. The rotational coupling interconnects the heating element with the housing.

20 Claims, 1 Drawing Sheet

METHOD AND APPARATUS FOR ADJUSTING THE RATE OF VAPORIZATION

CROSS REFERENCE TO RELATED APPLICATIONS

This is a non-provisional application based upon U.S. provisional patent application Ser. No. 60/578,663, entitled "A METHOD AND APPARATUS FOR ADJUSTING THE RATE OF VAPORIZATION", filed Jun. 10, 2004.

BACKGROUND OF THE INVENTION

1. Field of the Invention

The present invention relates to wicked vaporization systems, and, more particularly, to wicked vaporization systems using a heating element.

2. Description of the Related Art

An electrically heated chemical delivery system, which is connectable with an electrical receptacle is known. For example, it is known to provide a housing which directly carries a pair of terminals, which extend therefrom and may be plugged into a conventional 115 volt electrical receptacle. The electrical terminals are electrically connected to a heater disposed within the body of the delivery system. A heat actuated chemical is disposed within the body and releases its gasses into the ambient environment with heat accelerating the release.

One method used to alter the amount of vaporizable material that is released in the environment is to control the air flow around the heating element. Controlling the air flow requires adjustable elements in the housing to alter the air flow that passes by the vaporizable material.

Another method of controlling the vaporization of the vaporizable material is alter the heat supplied by way of the heating element. This requires control electronics, which add substantial cost to the assembly.

What is needed in the art is a way to adjust the vaporization rate in a simple cost effective manner.

SUMMARY OF THE INVENTION

The present invention provides a vaporization system that adjusts the amount of heat applied to the vaporizable material without altering the amount of power consumed by the device.

The invention comprises, in one form thereof, a vaporization device including a housing, a wick, at least one heating element and a rotational coupling. The wick is partially contained within the housing and extends from the housing. The at least one heating element being proximate the wick. The rotational coupling interconnects the heating element with the housing.

An advantage of the present invention is that heat to the wick is adjustable without the need to alter the power supplied to the resistive heater.

Another advantage of the present invention is that the vaporization rate of liquid from the wick is adjustable without controlling the airflow around the wick.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
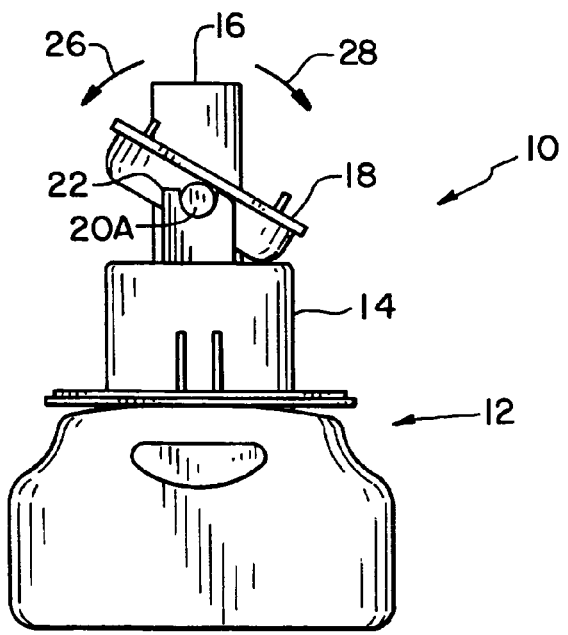
FIG. 1 is a side view of an embodiment of a vaporization device of the present invention.
Figure 2:
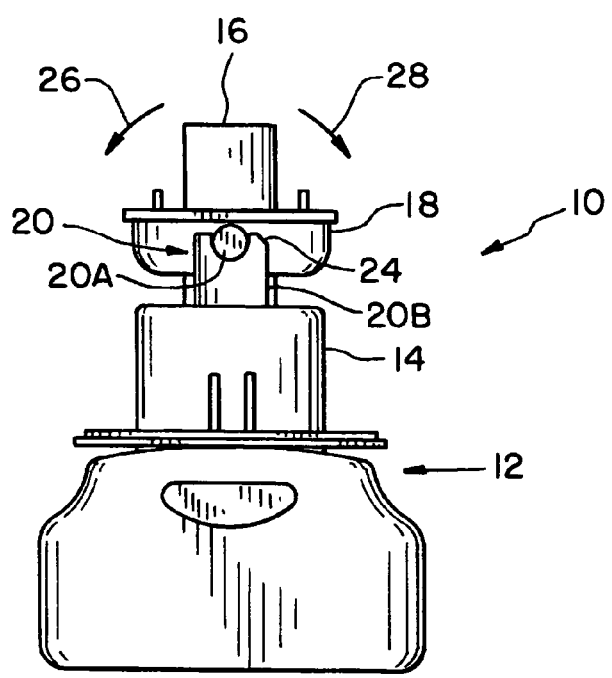
FIG. 2 is another side view of the vaporization device of FIG. 1.

Referring now to the drawings, and more particularly to FIGS. 1 and 2, there is shown a vaporization device 10 which generally includes a housing 12 having a reservoir 14, a wick 16 and a heating block 18 carrying one or more heating elements rotatably coupled to housing 12 by way of a rotational coupling 20. Housing 12 may include electrical contacts for an interconnection with an electrical supply that provides energy to heating block 18. Within housing 12 is a reservoir 14, which contains vaporizable material, which may be in the form of a fluid fragrance, an insecticide, a medicine or other material that is desirable to release in the air. The vaporizable material wicks up wick 16 from reservoir 14 and is in contact with ambient air. In order to accelerate the vaporization of the vaporizable material, heating block 18 supplies heat to wick 16 thereby increasing the vaporization of the vaporizable material supplied to wick 16 from reservoir 14.

Heating block 18 is rotatably coupled by way of rotational coupling 20 to housing 12. Rotational coupling 20 includes a pivot pin 20A associated with heating block 18 and a recessed flange 20B associated with housing 12. Pivot pin 20A of rotational coupling 20 is snapped into recessed flange 20B, thereby allowing heating block 18 to be easily coupled to housing 12. Heating block 18 may include more than one heating element, such as one located on each side of wick 16. Heating block 18 has a heated surface or circuit that is longer than the width of wick 16, thereby allowing heating block 18 to increase the heat transfer to wick 16 when heating block 18 is rotated as shown in FIG. 1. When heating block 18 is rotated, as shown in FIG. 2, the minimal amount of contact of heating block 18 with wick 16 is achieved, thereby having the lowest heat transfer from heating block 18 to wick 16. This results in a minimal amount of vaporization of the vaporizable material from wick 16.

Proximate to rotational coupling 20 is a stop 22 and a lowered stop 24. When heating block 18 is rotated in direction 26, an edge of heating block 18 contacts stop 22, thereby increasing the contact of heating block 18 with wick 16, which increase the heat transfer to wick 16. When heating block 18 is rotated in direction 28, until it encounters lowered stop 24, then an even higher amount of heat is transferred from heating block 18 to wick 16, since the angle of rotation in direction 28 is larger than the angle of rotation in direction 26. The rotation of heating block 18 is about an axis, which is normal to a surface of wick 16. Even though rotational coupling 20 is shown centrally disposed along the length of heating block 18, rotational coupling 20 may be located at a different location along heating block 18. As heating block 18 is rotationally displaced from the position, as shown in FIG. 2, the heat transfer to wick 16 is increased, because a greater length of the heating elements in heating block 18 are transferring heat to wick 16.

Both linear and non-linear heating elements are contemplated for use in vaporization device 10 in order to change the rate of increase of heat transfer to wick 16 as heating block 18 is rotated in either direction 26 or 28.

Advantageously, the present invention alters the heat flow to wick 16, thereby varying the temperature of wick 16. The vaporization of chemicals that are contained in wick 16 increases with the temperature of wick 16. The present invention simply adjusts the heat transfer by altering the contact of heating block 18 with wick 16, rather than using another device to adjust the power supplied to a heating element. This simple solution reduces the cost involved in having an adjustable vaporization rate device as compared with other methods of adjustment.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A vaporization device, comprising:
   a housing;
   a wick partially contained within said housing, said wick extending from said housing, said wick having a surface;
   at least one heating element proximate said wick; and
   a rotational coupling interconnecting said heating element with said housing, said rotational coupling having an axis substantially normal to said surface of said wick, said heating element being rotatable about said axis while said heating element is energized.

2. The vaporization device of claim 1, wherein altering a rotatable position of said at least one heating element about said rotational coupling alters an amount of heat transfer from said at least one heating element to said wick, thereby altering a vaporization rate of a vaporizable material in said wick.

3. The vaporization device of claim 2, further comprising a reservoir into which said wick is routed to convey said vaporizable material toward said at least one heating element.

4. The vaporization device of claim 3, wherein said reservoir is connected to a portion of said rotational coupling.

5. The vaporization device of claim 4, wherein said at least one heating element has a length and said wick has a width, said length being greater than said width.

6. The vaporization device of claim 5, wherein said at least one heating element is rotatable about said rotational coupling to a position such that said length of said at least one heating element is substantially in contact with said wick.

7. The vaporization device of claim 2, wherein said at least one heating element has a rotatable position with a minimum contact with said wick, said at least one heating element is rotatable through a first angle in a first direction from said rotatable position with minimum contact and a second angle in a second direction from said rotatable position with minimum contact, said first angle being larger than said second angle.

8. The vaporization device of claim 1, wherein said rotational coupling rotates about an axis that is substantially normal to said wick.

9. A vaporization device, comprising:
   a housing;
   a wick routed through a portion of said housing, said wick having a surface;
   a rotational coupling associated with said housing, said rotational coupling being rotatable about an axis substantially perpendicular to said surface of said wick; and
   at least one heating element pivotally associated with said wick about said rotational coupling, said at least one heating element being pivotable while energized.

10. The vaporization device of claim 9, wherein altering a rotatable position of said at least one heating element about said rotational coupling alters an amount of heat transfer to said wick, thereby altering a vaporization rate of a vaporizable material in said wick.

11. The vaporization device of claim 10, further comprising a reservoir in said housing into which said wick is routed to convey said vaporizable material to said at least one heating element.

12. The vaporization device of claim 11, wherein said at least one heating element has a length and said wick has a width, said length being greater than said width.

13. The vaporization device of claim 12, wherein said at least one heating element is rotatable about said rotational coupling to a position such that said length of said at least one heating element is substantially in contact with said wick.

14. The vaporization device of claim 10, wherein said at least one heating element has a rotatable position with a minimum contact with said wick, said at least one heating element is rotatable through a first angle in a first direction from said rotatable position with minimum contact and a second angle in a second direction from said rotatable position with minimum contact, said first angle being larger than said second angle.

15. The vaporization device of claim 9, wherein said rotational coupling is rotated about an axis that is substantially normal to said wick.

16. A method of altering the vaporization rate of a vaporizable material from a wick, comprising the step of rotatably positioning a heating element about an axis that is substantially normal to the wick while said heating element is energized.

17. The method of claim 16, further comprising the step of supplying the vaporizable material to the wick from a reservoir.

18. The method of claim 16, wherein said rotatably positioning step alters the amount by which said heating element is in contact with the wick, thereby altering the vaporization rate of the vaporizable material.

19. The method of claim 18, wherein said heating element has a first rotatable position with a minimum contact with the wick, a second rotatable position against a first stop and a third rotatable position against a second stop, when said heating element is in said second rotatable position more heat transfers to the wick than when said heating element is in said first rotatable position, when said heating element is in said third rotatable position more heat transfers to the wick than when said heating element is in said second rotatable position.

20. The method of claim 16, wherein said heating element has a length that is greater than a width of the wick.

* * * * *